US012734261B2

(12) United States Patent
Hood et al.

(10) Patent No.: US 12,734,261 B2
(45) Date of Patent: Sep. 15, 2026

(54) LIGHT EMITTING DEVICE EMITTING UV-C RADIATION AT DIFFERENT WAVELENGTHS UPWARD AND DOWNWARD

(71) Applicants: William Hood, Lake Bluff, IL (US); Chase Hood, Barrington, IL (US)

(72) Inventors: William Hood, Lake Bluff, IL (US); Chase Hood, Barrington, IL (US)

(73) Assignee: Cyclean, Inc., Buffalo Grove, IL (US)

( * ) Notice: Subject to any disclaimer, the term of this patent is extended or adjusted under 35 U.S.C. 154(b) by 794 days.

(21) Appl. No.: 17/820,875

(22) Filed: Aug. 18, 2022

(65) Prior Publication Data

US 2023/0056649 A1 Feb. 23, 2023

Related U.S. Application Data

(60) Provisional application No. 63/234,345, filed on Aug. 18, 2021.

(51) Int. Cl.

*A61L 2/10* (2026.01)
*H05B 47/11* (2020.01)
*H05B 47/115* (2020.01)
*A61L 103/75* (2026.01)

(52) U.S. Cl.

CPC ................ *A61L 2/10* (2013.01); *H05B 47/11* (2020.01); *H05B 47/115* (2020.01); *A61L 2103/75* (2026.01); *A61L 2202/11* (2013.01)

(58) Field of Classification Search

CPC .......... G09F 17/00; G09F 11/10; F21V 21/30; F21V 9/08; F21V 14/08; F21V 17/02; F21V 17/105; F21W 2131/406

See application file for complete search history.

(56) References Cited

U.S. PATENT DOCUMENTS

| | | | | |
|---|---|---|---|---|
| 11,184,967 | B2 | 11/2021 | Coleman | |
| 2017/0246331 | A1* | 8/2017 | Lloyd | A61L 2/10 |
| 2021/0085810 | A1* | 3/2021 | Barron | A61L 2/10 |
| 2021/0112647 | A1* | 4/2021 | Coleman | F21V 14/02 |
| 2021/0322597 | A1* | 10/2021 | Tu | H05B 47/20 |
| 2022/0086988 | A1 | 3/2022 | Coleman | |
| 2022/0331473 | A1* | 10/2022 | Gilling | G07C 9/00571 |
| 2024/0130825 | A1* | 4/2024 | Walen | A61B 90/08 |

FOREIGN PATENT DOCUMENTS

WO WO-2009151869 A2 * 12/2019 ....... G02F 1/133605

* cited by examiner

*Primary Examiner* — Sonji N Johnson

(57) ABSTRACT

In one embodiment, a light emitting device comprises one or more first light sources emitting UV-C light downward to irradiate the environment below the light emitting device (such as air and the floor and other surfaces). In another embodiment, the light emitting device comprises one or more second light sources emitting UV-C light of a different peak wavelength than the first light sources oriented to emit light upward to irradiate the environment above the light emitting device (such as air, the ceiling, and other surfaces). In one embodiment, one or more first light sources and the one or more second light sources emit light at different, independent duty cycles.

18 Claims, 2 Drawing Sheets

100
x
z
101
102
105
103
104
105
101
102
103

100
x
y 205
212
202

206
X
Z
204
103
201
207
200
211

LIGHT EMITTING DEVICE EMITTING UV-C RADIATION AT DIFFERENT WAVELENGTHS UPWARD AND DOWNWARD

CROSS REFERENCE TO RELATED APPLICATION

This application claims the benefit of U.S. Provisional Application No. 63/234,345, entitled "Short wave ultraviolet light emitting device," filed on Aug. 18, 2021, the entire contents of which are incorporated by reference herein.

BACKGROUND

The subject matter disclosed herein generally relates to light emitting devices such as light fixtures, light bulbs, replacement light bulbs, or devices comprising ultraviolet light emitting devices, and their components and method of manufacture. Light emitting devices are needed that emit light at wavelengths that efficiently and safely inactivate and/or reduce pathogenic bioburden in areas.

DETAILED DESCRIPTION OF THE INVENTION

Figures 1, 2:
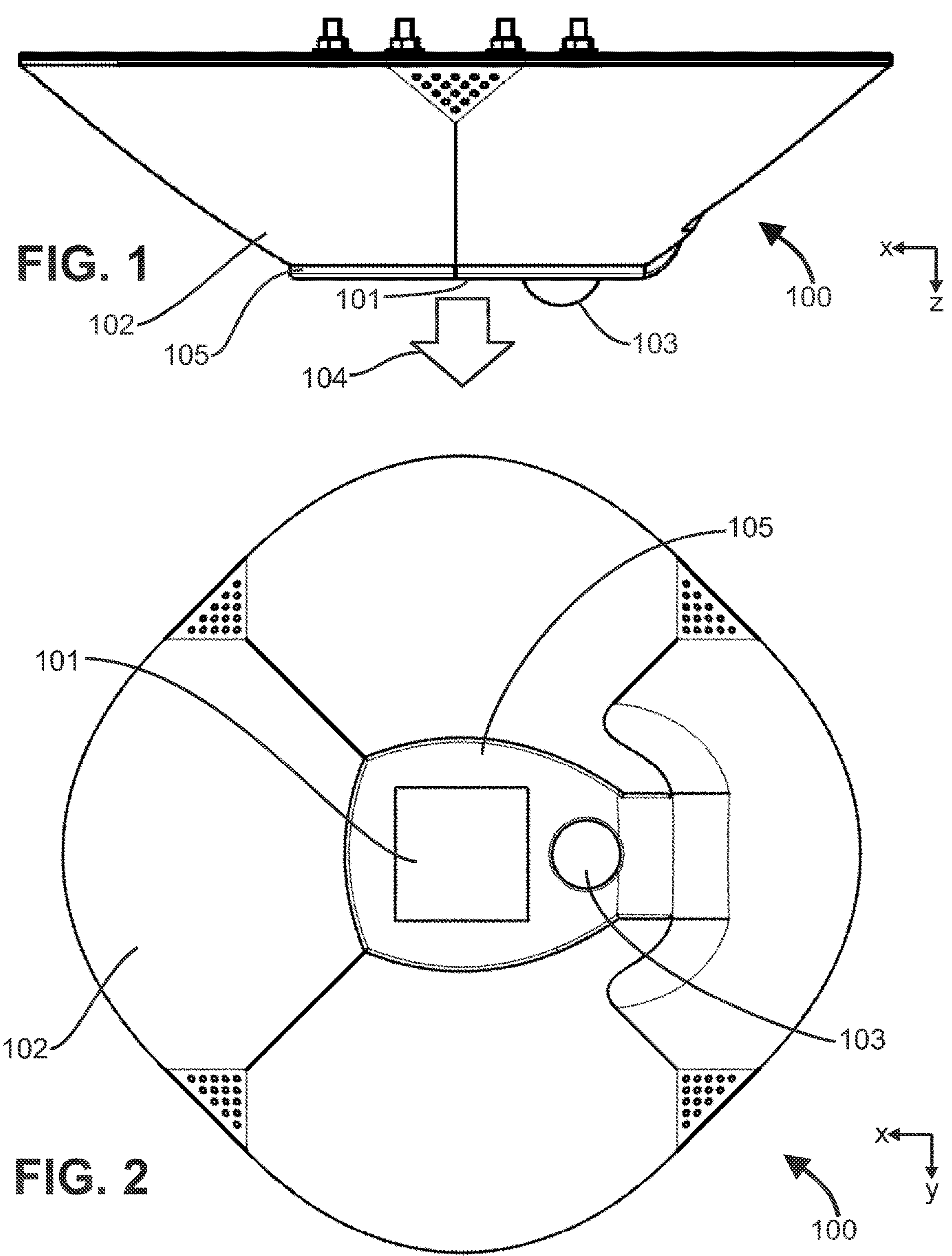
FIG. 1 is a side view of a light emitting device comprising a UV-C light source comprising one or more first light sources emitting UV-C light downward when the light emitting device is mounted to a ceiling.
FIG. 2 is a bottom view of the light emitting device of FIG. 1.

The features and other details of several embodiments will now be more particularly described. It will be understood that particular embodiments described herein are shown by way of illustration and not as limitations. The principal features can be employed in various embodiments without departing from the scope of any particular embodiment. The present inventive subject matter now will be described more fully hereinafter with reference to the accompanying drawings, in which embodiments of the inventive subject matter are shown. However, this inventive subject matter should not be construed as limited to the embodiments set forth herein. Rather, these embodiments are provided so that this disclosure will be thorough and complete, and will fully convey the scope of the inventive subject matter to those skilled in the art. Like numbers refer to like elements throughout. As used herein the term "and/or" includes any and all combinations of one or more of the associated listed items.

The terminology used herein is for the purpose of describing particular embodiments only and is not intended to be limiting of the inventive subject matter. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

When an element such as a layer, region or substrate is referred to herein as being "on" or extending "onto" another element, it can be directly on or extend directly onto the other element or intervening elements may also be present. In contrast, when an element is referred to herein as being "directly on" or extending "directly onto" another element, there are no intervening elements present. Also, when an element is referred to herein as being "connected" or "coupled" to another element, it can be directly connected or coupled to the other element or intervening elements may be present. In contrast, when an element is referred to herein as being "directly connected" or "directly coupled" to another element, there are no intervening elements present. In addition, a statement that a first element is "on" a second element is synonymous with a statement that the second element is "on" the first element.

Although the terms "first", "second", etc. may be used herein to describe various elements, components, regions, layers, sections and/or parameters, these elements, components, regions, layers, sections and/or parameters should not be limited by these terms. These terms are only used to distinguish one element, component, region, layer, section, or property from another region, layer, section, or property. Thus, a first element, component, region, layer, section, or property discussed below could be termed a second element, component, region, layer, section, or property without departing from the teachings of the present inventive subject matter.

Furthermore, relative terms, such as "lower" or "bottom" and "upper" or "top," may be used herein to describe one element's relationship to another element as illustrated in the Figures or description. Such relative terms are intended to encompass different orientations of the device in addition to the orientation depicted in the Figures. For example, if the device in the Figures is turned over, elements described as being on the "lower" or "bottom" side of other elements would then be oriented on the "upper" or "top" sides of the other elements. The exemplary term "lower", can therefore, encompass both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below. Likewise, "lower side" and "upper side" can therefore, encompass both an orientation of "lower side" and "upper side," depending on the particular orientation of the figure.

As used herein "Ultraviolet C" or "UV-C" radiation is radiation within a wavelength range of 100 nanometers to 280 nanometers, "nm" is an abbreviation of nanometers, and "mW" is an abbreviation for milliwatts.

Light Emitting Device

In one embodiment, a light emitting device is constructed to emit UV-C radiation downward into a room to inactivate and/or reduce pathogenic bioburden in the environment such as a room. In a further embodiment, the light emitting device emits UV-C radiation upward toward a ceiling. In one embodiment, a light emitting device emits UV-C radiation downward with a first peak wavelength and UV-C radiation upward with a second peak wavelength different than the first wavelength. For example, in one embodiment, a light fixture installed to or within the ceiling emits light with a peak wavelength at 222 nm downward, emits light with a peak wavelength at 254 nm upward, or emits light with a peak wavelength at 222 nm downward and emits light with a peak wavelength of 254 nm upward.

Light Source

In one embodiment, a light emitting device comprises one or more light sources selected from the group excimer lamp, microcavity microplasma excimer lamp, pulsed xenon lamp, light emitting diode, low pressure mercury lamp (standard output quartz, high output quartz, compact quartz or soft-glass), UV amalgam lamp, medium pressure UV lamp, low-pressure mercury lamp, gas-discharge lamp, laser, and solid state laser that produces UV-C light and/or light at other wavelengths disclosed herein. In one embodiment, the light source may comprise one or more optical wavelength filters to reduce the light output in one or more wavelength bands (such as visible, UV-A, and/or UV-B bands, for example).

For example, suitable light sources emitting UV-C light (such as 222 nm) include micro-cavity plasma arrays comprising one or more noble gases, one or more halogen gases, or a mixture of at least one halogen gas with one or more noble gases, such as those disclosed in U.S. Pat. No. 11,004,673, and light sources disclosed in US Patent Publication Nos. 20110275272, 20120319559, 20130071297, and International PCT Application Publication No. WO2007011865, the entire contents of each are incorporated by reference herein.

In another embodiment, the one or more light sources include one or more arrays of light sources (such as light emitting diodes or microcavities of plasma) which may be mounted on linear circuit boards or substrates. In one embodiment, the light emitting device comprises one or more linear sections of circuit boards or substrates with discrete UV-C LED packages (which comprise at least one UV-C LED die) and/or microcavities of plasma. In another embodiment, a light emitting device comprises a plurality of light sources within one package disposed to emit light toward a surface for illumination. In one embodiment, the light emitting device comprises at least one selected from the group of: 2, 3, 4, 5, 6, 8, 9, 10, 20, 40, 60, 80, 100, 120, 140, 160, 180, 200, 220, 240, 260, 280, 300, 320, 340, 360, 380, and 400 light sources, light emitting diodes, or microcavities of plasma. In one embodiment, the average dimension, A, of the LEDs in one or more linear arrays of LEDs in a linear direction is less than one selected from the group of 10 mm, 8 mm, 6 mm, 5 mm, 4 mm, 3 mm, and 2 mm. In one embodiment, the light emitting device comprises one or more LEDs of package or case type selected from the group: 0402, 0404, 0603, 0604, 0605, 0606, 0802, 0805, 0806, 0807, 1008, 1050, 1104, 1106, 1204, 1205, 1206, 1208, 1209, 1210, 1305, 1307, 1308, 1411, 1412, 1505, 1608, 1610, 1612, 1616, 1810, 1819, 1908, 1916, 2012, 2024, 2106, 2120, 2122, 2214, 2221, 2220, 2432, 2508, 2520, 2810, 2832, 3010, 3015, 3020, 3022, 3025, 3028, 3034, 3107, 3122, 3228, 3210, 3216, 3224, 3228, 3430, 3519, 3528, 3528, 3632, 4028, 4040, 4234, 4238, 4242, 5050, 5630, 6050, and 7950 where the first two numbers typically represent the length and the second two numbers represent the width in tenths of millimeters. For example, the 5630 LED package type has a length of 5.6 millimeters and a width of 3 millimeters.

Spectral Properties of the One or More Light Sources

In one embodiment, the light emitting device comprises one or more light sources arranged to emit UV-C light with the same or different first peak wavelength, first center wavelength, first average wavelength, and first wavelength bandwidth upward and/or downward when the light emitting device is mounted in the upper region of a room. In this embodiment, the one or more light sources may have a first peak wavelength, first center wavelength, or first average wavelength selected from the group: 218 nm, 219 nm, 220 nm, 221 nm, 222 nm, 223 nm, 224 nm, 225 nm, 226 nm, 193 nm, 248 nm, 308 nm, 351 nm, and 282 nm. In one embodiment, the one or more light sources may have a first peak wavelength, first center wavelength, or first average wavelength within the wavelength range of 100 nm to 280 nm, 150 nm to 250 nm, 200 nm to 250 nm, 215 nm to 250 nm, 215 nm to 230 nm, 220 nm to 225 nm, and 221 nm and 223 nm. In one embodiment, the one or more light sources emit light with the same or different wavelength bandwidths (full wavelength bandwidth at half maximum intensity) less than, equal to, or greater than one selected from the group: 1 nm, 2 nm, 3 nm, 4 nm, 5 nm, 10 nm, 15 nm, 20 nm, 25 nm, 30 nm, 40 nm, 50 nm, and 70 nm.

In one embodiment, the light emitting device comprises one or more first light sources emitting UV-C light downward to irradiate the environment below the light emitting device (such as air and the floor and other surfaces) and optionally a second light source emitting UV-C light upward to irradiate the environment above the light emitting device (such as air, the ceiling, and other surfaces). In this embodiment, the one or more first light sources may emit light with a first peak wavelength, first center wavelength, or first average wavelength (222 nm for example) and the one or more second light sources may emit light with a second peak wavelength, second center wavelength, or second average wavelength different from the first peak wavelength, first center wavelength, or first average wavelength, respectively, (254 nm for example). In one embodiment, a method of inactivating and/or reducing pathogenic bioburden in an environment comprises emitting first UV-C light (such as 222 nm light for example) from one or more first light sources in a light emitting device downward to irradiate the environment below the light emitting device (such as air and the floor and other surfaces) and optionally emitting UV-C light (that may have a different peak wavelength, center wavelength, or average wavelength than the first UV-C light, (such as 254 nm for example) from one or more second light sources to irradiate the environment above the light emitting device (such as air, the ceiling, and other surfaces).

In some embodiments, the light emitting device comprises only one or more light sources emitting light downward when the light emitting device is positioned in room or mounted to or near the ceiling, for example. In one embodiment, the one or more second light sources may have a second peak wavelength, second center wavelength, or second average wavelength selected from the group: 218 nm, 219 nm, 220 nm, 221 nm, 222 nm, 223 nm, 224 nm, 225 nm, 226 nm, 193 nm, 248 nm, 265 nm, 273 nm, and 280 nm. In one embodiment, the one or more second light sources may have a second peak wavelength, second center wavelength, or second average wavelength within the wavelength range of 100 nm to 280 nm, 150 nm to 250 nm, 200 nm to 250 nm, 215 nm to 250 nm, 215 nm to 230 nm, 220 nm to 225 nm, and 221 nm and 223 nm, 230 nm to 240 nm, 240 nm to 250 nm, 250 nm to 260 nm, and 252 nm to 258 nm. In one embodiment, the one or more second light sources emit light with the same or different wavelength bandwidths (full wavelength bandwidth at half maximum intensity) at less than, equal to, or greater than one selected from the group: 1 nm, 2 nm, 3 nm, 4 nm, 5 nm, 10 nm, 15 nm, 20 nm, 25 nm, 30 nm, 40 nm, 50 nm, and 70 nm.

In one embodiment, the light emitting device comprises one or more visible light sources that may be used to indicate a status of the light emitting device and/or light source or to provide a visible representation of the angular light spread from the invisible UV-C light emitting downwards and/or upwards. In one embodiment, the angular full-width at half maximum luminous intensity of the one or more visible light sources in one or two orthogonal planes of light including the nadir (or orthogonal to the light emitting surface of the light emitting device) is within 5%, 10%, 15%, or 20% of the angular full-width at half maximum radiant intensity of the light from the one or more first light sources (such as UV-C light sources) in the same one or two orthogonal planes. In another embodiment, the angles at which the visible light intensity from the one or more visible light sources is less than 5% of the maximum visible light intensity in the one or two orthogonal planes of light including the nadir (or orthogonal to the light emitting surface of the light emitting device) are within 5%, 10%, 15%, or 20% of the angles at which the radiant intensity from the one or more first light sources (such as UV-C emitting light sources) is less than 5% of the maximum radiant light intensity in the same one or two orthogonal planes. In some embodiments, the angular bandwidth and/or angular cut-off angles of the visible light is matched to the UV-C light to visibly represent the illumination from the UV-C light, such that the visible light may be turned on (such as in a visible light representation mode) to illuminate the room to indicate which areas and/or surfaces would receive more or less UV-C light (including indicating shadow areas) without risk to UV-C exposure and/or additional UV-C exposure.

In one embodiment, the light emitting device comprises an indicator light source that emits visible light. In one embodiment, the light emitting device comprises one or more light sources that emits visible light to provide illumination in addition to one or more light sources emitting UV-C light. In one embodiment, a light emitting device comprises at least one broadband light source that emits light in a wavelength spectrum larger than 100 nanometers. In another embodiment, a light emitting device comprises at least one narrowband light source that emits light in a narrow bandwidth less than 100 nanometers. In another embodiment, a light emitting device comprises at least one broadband light source that emits light in a wavelength spectrum larger than 100 nanometers or at least one narrowband light source that emits light in a narrow bandwidth less than 100 nanometers. In one embodiment a light emitting device comprises at least one narrowband light source with a peak wavelength within a range selected from the group of 300 nm-350 nm, 350 nm-400 nm, 400 nm-450 nm, 450 nm-500 nm, 500 nm-550 nm, 550 nm-600 nm, 600 nm-650 nm, 650 nm-700 nm, 700 nm-750 nm, 750 nm-800 nm, and 800 nm-1200 nm. The light sources may be chosen to match the spectral qualities of red, green and blue such that collectively when used in a light emitting device, the color may be dialed in to achieve a desired color. In one embodiment, at least one light source is an LED package comprising a red, green, and blue LED capable of emitting light with a white color when each are emitting light. In another embodiment, the LED is a blue or ultraviolet LED combined with a phosphor. In another embodiment, a light emitting device comprises a light source with a first activating energy and a wavelength conversion material which converts a first portion of the first activating energy into a second wavelength different than the first. In another embodiment, the light emitting device comprises at least one wavelength conversion material selected from the group of a fluorophore, phosphor, a fluorescent dye, an inorganic phosphor, photonic bandgap material, a quantum dot material. In another embodiment, the light emitting device comprises white LED light sources. In another embodiment, the light sources comprise LEDs that are at least one selected from the group of: warm white, cool white, neutral white, daylight white, have a correlated color temperature between 2200 K and 2900 K, have a correlated color temperature between 2900 K and 3600 K, have a correlated color temperature between 3600 K and 4500 K, have a correlated color temperature between 4500 K and 4900 K, and have a correlated color temperature between 4900 K and 6600 K.

Radiant Light Flux Output

In one embodiment, the one or more first light sources and/or one or more second light sources each emit light with a radiant flux (or the collective total flux) within the range of one or more selected from the group: 0.1 mW to 2 mW, 0.1 mW to 1.5 mW, 0.5 mW to 1.5 mW, 1 mW to 1.5 mW, 1 mW to 10 mW, 1 mW to 200 mW, 5 mW to 50 mW, 10 mW to 40 mW, 15 mW to 35 mW, 20 mW to 35 mW, 30 mW to 40 mW, greater than 10 mW, greater than 20 mW, greater than 30 mW, greater than 40 mW, greater than 50 mW, greater than 75 mW, greater than 100 mW, greater than 200 mW, less than 10 mW, less than 20 mW, less than 30 mW, less than 40 mW, less than 50 mW, less than 75 mW, less than 100 mW, and less than 200 mW. In one embodiment the radiant flux output for each (or collectively from all) of the one or more first light sources directed downward (and optionally for the one or more second light sources directed upwards) may be chosen based at least in part on the light emitting device mounting height, distance from the ceiling, angular light output profile, recommended exposure limitations based on the wavelength and light output at surfaces, and/or exposure sufficient for inactivation and/or reduction of a particular amount and/or type of pathogenic bioburden at surfaces and/or areas or volumes based on a desired duty cycle, on-time, or other light emitting mode.

In one embodiment, the total radiant flux output from the one or more first light sources directed downward divided by the total radiant flux output from the one or more second light sources directed upward when all light sources are emitting light at the maximum power allowed by the light emitting device is one or more selected from the group: greater than 1, less than 1, equal to 1, between 0.1 and 0.8, between 0.5 and 1, between 0.7 and 0.9, between 0.4 and 0.9, between 0.1 and 0.5, between 0.01 and 0.3, between 1 and 10, between 1 and 20, between 1 and 2, between 1 and 5, between 1 and 10, between 1 and 1.8, and between 1 and 1.5. In one embodiment, the ratio of the total maximum light output flux from the downward directed light to the upward directed light is chosen to optimize the inactivation and/or reduction in pathogenic bioburden for the upward and downward directed light while considering the safety due to exposure from the UV-C light in one or more light emitting modes of the light emitting device. In one embodiment, the above referenced ratio of the output flux is during an operational mode where both the one or more first light sources and the one or more second light sources are emitting light and the maximum light output is the maximum for a specific operational mode.

Angular Light Modifier

In one embodiment, the one or more first light sources and/or one or more second light sources includes one or more angular light modifiers selected from the group of: reflector, light baffle, diffuser, and UV fused silica diffuser. In one embodiment, the angular light modifier increases or decreases the angular light output of the light emitting device. The first peak wavelength, first center wavelength, first average wavelength, first wavelength bandwidth, first light flux output, first angular light modifier, the second peak wavelength, second center wavelength, second average wavelength, second wavelength bandwidth, second light flux output, and/or second angular light modifier may be chosen for a particular efficacy in inactivation or reduction of one or more specific pathogenic bioburden and in consideration of safety of exposure to humans for a particular installation and/or light emitting mode.

Air Flow

In one embodiment, the light emitting device comprises a fan or other air flow generation device (such as an electrostatic precipitator) that generates air flow across the first light flux or the second light flux from one or more UV-C light sources. In one embodiment, the air flow generation device, such as a fan, generates air flow across the first light flux and/or second light flux from the one or more UV-C light sources, such as directing the air flow across the first flux from the first light sources emitting light with a wavelength of 222 nanometers (in the downward direction, for example) and/or the second light flux from the one or more second light sources emitting light with a peak wavelength of 254 nanometers (in the upward direction, for example).

Controlling and Monitoring the Light Emitting Device

In one embodiment, control for the light emitting device is through a user interface at the light emitting device, remote from the light emitting device using a wired connection, or remote from the light emitting device using a wireless connection. In one embodiment, the light emitting device comprises a user interface for controlling the light emitting device at the light emitting device. In one embodiment, the user interface at the light emitting device comprises one or more user interface devices selected from the group: switch, dial, knob, button, pull cord/chain/string, touch sensitive switch or interface (such as a capacitive based touch-sensitive region of the device or a touchscreen, and microphone (for user commands, for example).

In another embodiment, the light emitting device comprises a wired control connection wherein one or more light output properties of the light emitting device is controlled using a wired connection to the light emitting device. In one embodiment, the control connection wired to the light emitting device comprises one or more remote operated wired control devices, such as a user interface (such as three flip switches) in a wall near a door, or a user interface on a wall (such as a light switch). In one embodiment, a system for controlling a light emitting device comprises a light emitting device and a control module comprising one or more user interfaces operatively configured to control the light output from the one or more first light sources and optionally, independently from the light output from the one or more second light sources of the emitting device.

In another embodiment, the light emitting device comprises a wireless control connection wherein one or more light output properties of the light emitting device are controlled using a wireless connection to the light emitting device. In one embodiment, the wireless control device wirelessly connected to the light emitting device comprises one or more remote operated wireless control devices, such as a wireless user interface device in a wall near a door, a wireless user interface remote from the light emitting device, or a portable device (such as controlling the light emitting device using an application on a wireless phone).

In one embodiment the light flux output of the one or more first light sources directed downward and/or the one or more second light sources directed upward (if provided) may be controlled or adjusted in a time period (optionally independently) using one or more light emitting modes selected from the group of: manual control, automatic control, programmed time control or schedule, duty cycle control, preset mode, another mode (such as manual mode) with control overridden based on input from a sensor (such as upward directed or downward directed motion sensor), test mode (such as visible light test mode that represents the UV-C light output), visible light illumination and UV-C light output mode, light flux output ratio for the one or more first light sources to the one or more second light sources, light source life maximizing mode that maximizes the lifetime of the one or more first light sources and/or one or more second light sources, maximum inactivation or reduction of pathogenic bioburden mode, optimized energy saving mode for a desired variable (such as exposure time, exposure intensity, or occupancy prediction/estimation, for example, such as mode uses the shortest exposure time for effective inactivation and/or reduction of pathogenic bioburden from light from the one or more first light sources and/or one or more second light sources to minimize electrical power consumed).

In one embodiment, the light emitting device comprises one or more microprocessors and at least one non-transitory computer-readable storage medium that collectively store the time duration (run time or counter) of emitting light of the one or more first light sources, and/or the one or more second light sources, and/or the light emitting device. In one embodiment, the light emitting device provides a visible (such as through a visible LED blinking or color change) indication, and/or audio indication, and/or visibly display indication through an application or software on a the light emitting device, portable device, remote server, remote computer, remote operating device, or remote building management computer system when the run time of the one or more first light sources, and/or the one or more second light sources, and/or the light emitting device reaches a time threshold. In one embodiment the time threshold is a threshold time less than one selected from the group of 40%, 30%, 20%, 15%, 10%, and 5% of the expected lifetime remaining for one or more of the first and/or second light sources. For example, in one embodiment, a red LED indicator emits red light downward when the duration of the 222 nm UV-C light source has reached a remaining lifetime of 20% of an expected lifetime of 3,000 hours. In one embodiment, the light emitting device comprises a button, a switch, dial, or a user input device of a system in communication with the light emitting device that resets the run time counter. In one embodiment, a side or the lower side of the light emitting device comprises one or more displays that indicate the number of hours the one or more first light sources and/or the one or more second light sources have been emitting light. In another embodiment an LED emits green, red, blue, white, or other color visible light when the light emitting device is emitting UV-C light.

In one embodiment, one or more light emitting devices which may be positioned or installed in one or more locations and/or buildings and may be controlled (and/or the light output, light emitting mode, or other status information may be determined) in one or more light emitting modes using one or more communication methods (optionally in communication with a remote device, remote server, remote web server, remote processor, or website) such as a wired ethernet connection to the light emitting device, or wireless radio communication to the light emitting device (such as an IEEE 802.11 protocol (Wi Fi), Bluetooth® protocol, Z-wave protocol, or Zigbee protocol, for example).

In one embodiment, the light-emitting device has a radio frequency transmitter and a receiver that receives and transmits information. In a further embodiment, the light emitting device changes a property due to radio frequency communication with a device. In one embodiment, the radio frequency transmitter transmits and receives the frequency-hopping spread spectrum radio technology. In another embodiment, the light-emitting device includes a radio transmitter and receiver that receives and transmits radiation by Gaussian frequency-shift keying (GFSK). In another embodiment, the light-emitting device has a short wavelength radio transmission protocol, such as Bluetooth® protocol, radio frequency transmitter and receiver that receives and transmits information. In another embodiment, the light-emitting device includes an IEEE 802.11 compliant radio transmitter and receiver. In another embodiment, the light-emitting device includes an IEEE 802.15.4-2003, ZigBee® RF4CE, or ZigBee® compliant radio transmitter and receiver. For example, in one embodiment, the light emitting device receives information from a wireless router using an IEEE 802.11 protocol that directs the light emitting device to change the light emitting mode, provide an update on the status of the light emitting device, or directly change the light flux output from the one or more first light sources directed downward and/or the one or more second light sources directed upward.

In another embodiment, the light-emitting device includes a radio transceiver compliant to at least one communication standard for creating a wide area network (WAN) selected from the group of: iBurst™, Fast Low-latency Access with Seamless Handoff-Orthogonal Frequency Division Multiplexing (Flash-OFDM™), Wi-Fi: 802.11 standard, WiMAX: 802.16 standard, UMTS over W-CDMA, UMTS-TDD, EV-DO x1 Rev 0, Rev A, Rev B and x3 standards, HSPA D and U standards, RTT, GPRS, and EDGE. In another embodiment, the light-emitting device includes a radio transceiver compliant to at least one communication standard for creating a local area network (WLAN) selected from the group of: IEEE 802.11-2007, IEEE 802.11a, IEEE 802.11b, IEEE 802.11g, IEEE 802.11n, and amended IEEE 802.11-2007 standards or protocols. In a further embodiment, the light-emitting device includes a radio transceiver compliant to at least one communication standard for creating a personal area network (WPAN) selected from the group of: short wavelength wireless transmission protocol, such as Bluetooth® protocol (including standard protocol and low energy protocol), high level communication protocol such as ZigBee® Wireless USB, UWB, IPv6 over Low power Wireless Personal Area Networks, ONE-NET™, Z-Wave®, and EnOcean® standards. In another embodiment, the light emitting device includes a transceiver disposed to receive and transmit radio frequency information over a cellular phone connection protocol selected from the group of: CDMA, GSM, EDGE, 3G, UMTS, and SMS. In another embodiment, the light-emitting device includes 2 or more radio frequency transceivers configured to receive similar or different protocols, such as Bluetooth® protocol and an IEEE 802.11 protocol, for example.

In one embodiment, the light-emitting device includes an infrared photodetector, a phototransistor or an infrared (IR) receiver disposed to receive IR light. For example, in one embodiment, the light flux output from the one or more first light sources directed downward and/or the one or more second light sources directed upward is increased, decreased, changed, or turned off in response to information received from or through an infrared receiver from an infrared remote control. In one embodiment, the light emitting device communicates with a second device used in a wired connection. In another embodiment, the connection between the light emitting device and the second device includes one or more of the following connections: serial, asynchronous serial, parallel, and USB. In one embodiment, the light emitting device communicates with a second device using one or more communication architectures, network protocols, data link layers, network layers, network layer management protocols, transport layers, session layers, and/or application layers.

In one embodiment, the light emitting device communicates with a building management or automation system (such as a computer network communicating using ASHRAE BACnet protocol, for example). In this embodiment, the light emitting device may be controlled and/or provide information to a building management system that can control the light emitting device according to one or more light emitting modes and/or instructions which can take into account information from other sensors in the system (such as motion detectors on light emitting devices just outside of a door to a room with the light emitting device comprising one or more UV-C light sources detecting movement and instructing the second light emitting device to stop emitting UV-C light from the one or more first light sources and/or the one or more second light sources.

In one embodiment, the light emitting device is controlled to adjust the radiant light flux of the one or more first light sources directed downward and/or the one or more second light sources directed upward using software operating on a processor on the light emitting device and/or remote from the light emitting device based on one or more input selected from the group: information from one or more sensors, initial input from the manufacturer, subsequent updated information from the manufacturer (such as a firmware or data update), user input and selections, user selection of one or more light emitting modes and associated parameters, using one or more default light emitting modes and default parameters, input information or light emitting mode selection or parameters from a third party (such as a building manager), input instructional, sensor, or parameter information from a network comprising building management software and/or other UV-C light emitting devices or light fixtures.

In one embodiment, a UV-C sensitive spot meter or UV-C sensitive imager is used to evaluate the UV-C irradiation at a particular location/area in the environment receiving UV-C light from the light emitting device. In one embodiment, the radiant flux output from the one or more first light sources directing light downward and/or the radiant flux output from the one or more second light sources directing light upward is adjusted based on input information from a UV-C spot meter or a UV-C imager. In one embodiment, a handheld UV-C spot meter, fixed location UV-C spot meter or detector (such as a UV-C spot meter attached to arm that attached to the light emitting device that may be swung out to receive UV-C light from the light emitting device and later rotated back to the housing), or UV-C imaging device is used in a UV-C illumination system comprising a UV-C light emitting device as disclosed herein and the output from the UV-C spot meter is manually or automatically, input (such as by using IEEE 802.11, Bluetooth, serial USB or other communication protocol, for example) into software or an application on the light emitting device or in communication with the light emitting device, such that the radiant light flux output from the one or more first light sources and/or the radiant light flux output from the one or more second light sources may be evaluated based on lifetime information, or manually or automatically adjusted. This manual or automatic adjustment may achieve a target radiant light flux output at the UV-C radiant intensity evaluation location, achieve a target overall light flux output, or achieve a specific target light flux output at another location based on relative known or input parameters. In one embodiment, the radiant light flux from the one or more first light sources or the one or more second light sources may be evaluated using the spot meter or UV-C imager, such as for example, to facilitate achieving a desired output radiant intensity and/or desired exposure. In one embodiment the light emitting device comprises a user adjustable light output knob, dial, slide, or other variable adjustment mechanism that can be adjusted to increase and/or decrease the radiant light flux output from the one or more first light sources oriented downward and/or the one or more second light sources oriented upward to achieve a specific radiant light flux output from the one or more first light sources and/or the one or more second light sources in real-time while a user is viewing a display, dial, or indicator of the UV-C spot meter or UV-C imager. In one embodiment, the UV-C imager is a CCD imager with a UV-C bandpass filter (and/or short pass filter or other filter that absorbs and/or reflects greater than 80% of light with wavelengths longer than 280 nm and a phosphor conversion layer that down converts incident 222 nm light to light of a longer wavelength such that the CCD can detect the UV-C light. In one embodiment a method of adjusting the light output from a light emitting device comprising one or more first light sources oriented downward and/or one or more second light sources oriented upward comprises adjusting (manually and/or automatically) the radiant light flux output of the one or more first light sources oriented downward and/or the one or more second light sources oriented upward (optionally independently) based on information from a UV spot meter and/or a UV-C imager which may be portable, an attachment or accessory to a portable device such as a cellphone, in a fixed location (in the environment or on the light emitting device), or on an arm or extension of the light emitting device that may be translated and/or rotated into the UV-C light output from the light emitting device.

Other Components of the Light Emitting Device

In one embodiment, the light emitting device comprises one or more power supplies, AC/DC converters, control circuits, communication modules, radio transceiver, wiring, housing, connectors, switches, dials, buttons, light source access panel, or other devices known to be used in UV-C light irradiation devices and/or visible light illumination devices irradiating and/or illuminating a room or area.

In one embodiment, the light emitting device is powered by an electrical signal selected from the group of 12V DC, 12V AC, 110-277V AC, 220-240V AC, switchable power supply, 28V DC power supply, AC power supply, DC power supply, and 3V DC power supply. In another embodiment, the light emitting device has a backup battery based power supply.

Light Source Access

In one embodiment, the light emitting device comprises a housing comprising the one or more first light sources and/or the one or more second light sources. In one embodiment, the housing has an access panel, access door, access flap, or access opening to permit access from beneath the light emitting device (such as an overhead light fixture) when installed such that the light source may be changed. In one embodiment, the one or more first light sources and/or the one or more second light sources are bulbs or field replaceable light sources. In this embodiment, the one or more power supplies may be optionally replaceable.

Sensors

In one embodiment, the light emitting device comprises one or more active or passive proximity sensors, occupancy sensors, or motion detectors positioned to detect motion beneath and/or above the light emitting device. In one embodiment, the one or more proximity sensors, occupancy sensors, or motion detectors are one or more selected from the group: infrared sensor, capacitive sensor, photoelectric sensor, doppler effect sensor, CCD sensor, CMOS sensor, ultrasonic sensor, microwave sensor, tomographic motion detector. In one embodiment, the light emitting device comprises two or more different active or passive proximity sensors, occupancy sensors, or motion detectors to increase accuracy. In one embodiment the light from the one or more first light sources directed downward is turned off or on when motion or occupancy is detected beneath the light emitting device. In another embodiment the light from the one or more second light sources directed upward is turned off or on when motion or occupancy is detected above the light emitting device. In one embodiment, the light emitting device comprises a UV imager that captures images representing relative values or calibrated absolute values of light reflected from the environment below (and optionally a second UV imager capturing from above) from which UV-C intensity and/or exposure can be estimated and/or calculated optionally with input from a user of the materials of the exposed surface (such as aluminum or wood) or the UV-C reflectances (at the wavelengths of the corresponding light sources) of the materials (which may be looked up in a data table by the software for the calculations). In this embodiment, a user may, for example, see on a display an image representing the specific UV-C exposure at the surfaces of the area (optionally using a false color map) which may indicate shadow areas, for example. In another embodiment, the light emitting device comprises a visible light imager which captures a visible light image of the environment, upon which an overlay of the UV-C exposure may be overlaid in a false-color map or other visible indication on the display.

Other Components of the Light Emitting Device

In one embodiment, the light emitting device or system comprising a light emitting device comprises one or more selected from the group: power supply, driver, battery, photovoltaic cell, photosensor (for detecting ambient light levels or change in light output or color from LEDs over time, for example), occupancy sensor, infrared light sensor, microphone, speaker, alarm, smoke detector, carbon monoxide detector, radio transceiver, microcontroller, non-transitory computer-readable storage medium, and communication interface port (such an RJ11, RJ45, USB, mini-USB, or other electronic device communication transfer port, for example). In one embodiment, the light emitting device comprises an occupancy sensor or door sensor (such as a magnetic door sensor) or is electrically or communicatively coupled to the sensor such that the light emitting device stops or starts emitting UV-C light when movement is detected, the door is opened, or occupancy is otherwise detected. In one embodiment, the portable device and/or vehicle comprise one or more processors (such as microprocessors) operatively configured to execute one or more algorithms, analyze information, communicate information, and/or execute one or more operational or light emitting modes for the light emitting device or system comprising the light emitting device. One or more algorithms disclosed herein may be executed on one or more processors of the light emitting device, portable device, or a remote device (such as a remote server). In one embodiment, the light emitting device, portable device, or remote device comprises software or software components executing one or more algorithms. The software and/or data may be stored on one or more non-transitory computer-readable storage media. The software may be the operating system or any installed software or applications, or software, applications, or algorithms stored on a non-transitory computer-readable storage medium of the light emitting device, portable device, and/or remote device.

Light Emitting Device Type and Location

In one embodiment, the light emitting device is a light fixture or replacement bulb. In one embodiment, the light emitting device is a light fixture, can light, troffer light, cove light, recessed light, torch lamp, floor lamp, chandelier, surface mounted light, pendant light, sconce, track light, under-cabinet light, emergency light, wall-socket light, exit light, high bay light, low bay light, strip light, building light, outdoor light, accent light, flood light, wall-washer light, wall light, ceiling light, ceiling fan light, car light, outdoor flood light, or vehicle light. In one embodiment, the light emitting device is used in one or more selected from the group: an educational facility, hotel, restaurant, emergency room, doctor or dentist office, department of motor vehicle location, government office or public location, airport, dock, healthcare facility, retail location, workout facility or gym, gym shower, meat-packing facility, poultry packing facility, food processing facility, theater, transit or transportation facility (such as a train or commuter rail or subway facility and/or their indoor or outdoor platforms) and office.

In one embodiment, the light emitting device or a system comprising the light emitting device comprises one or more selected from the group: mounts, accessories, fasteners, other components such as a stem kit, swivel ball hanger, T-bar box hanger for 2 foot by 2 foot mounting, and grid clips (such as grid clips for T-bars or suspended ceiling components) to enable the light emitting device to be attached to a common light fixture installation location, junction box, downlight light fixture can, box mounting clip.

Shape of Light Emitting Device

In one embodiment, the light emitting device is substantially planar in a plane substantially orthogonal to the optical axis (or nadir of the light emitting device) of the one or more first light sources oriented downward. In one embodiment, the light emitting device is substantially linear (with a dimension in one first direction orthogonal to the optical axis (or nadir of the light emitting device) of the one or more first light sources oriented downward more than 3 times the dimension of the light emitting device in a second direction orthogonal to the first direction and the optical axis (or nadir of the light emitting device) of the one or more first light sources oriented downward. In one embodiment, the light emitting device is hemispherical or protrudes outward in a direction parallel to the optical axis (or nadir of the light emitting device) of the one or more first light sources oriented downward. In one embodiment, the light emitting device is in the shape of a rectangular cuboid, an apex-truncated square pyramid, or a prismatoid.

Waterproof

In one embodiment, the light source and electrical components are substantially sealed by at least one of an epoxy, resin, rubber, silicone, or polymer such that the electrical components are waterproof to a depth selected from the group of 5 feet, 10 feet, 20 feet, 30 feet, 50 feet, 100 feet, and 200 feet. This can be useful, for example, in facilities with large numbers of people with surfaces that must be cleaned regularly or in environments where the light emitting device (such as a ceiling mounted light fixture) may be exposed to water, moisture, or high humidity, such as a gym shower, meat-packing facility, poultry packing facility, food processing facility, or outdoor train platform, for example. In another embodiment, the light emitting device components satisfy the United Laboratories UYMR2 standards for components and fittings intended for use in electric signs and accessories. In another embodiment, the light emitting device continues to operate after a 12 hour continuous salt spray test. In another embodiment, the light emitting device continues to operate after a 24 hour continuous salt spray test. In one embodiment, the light emitting device continues to operate after a 48 hour continuous salt spray test. In one embodiment, the light emitting device continues to operate after a 60 hour saltwater soak test. In one embodiment, the light emitting device continues to operate after a 120 hour saltwater soak test. In another embodiment, the light emitting device continues to operate after a 240 hour saltwater soak test.

The following are more detailed descriptions of various embodiments illustrated in the Figures.

FIG. 1 is a side view of a light emitting device 100 comprising a UV-C light source 101 comprising one or more first light sources emitting UV-C light 104 downward when the light emitting device is mounted to a ceiling. The light emitting device 100 further comprises an occupancy sensor 103, a housing 102, and an access door 105 to enable access to the UV-C light source 101 to enable user replacement of the UV-C light source 101 from beneath the light emitting device 100. In one embodiment, the one or more first light sources emit 222 nm light.

FIG. 2 is a bottom view of the light emitting device 100 of FIG. 1.

Figure 3:
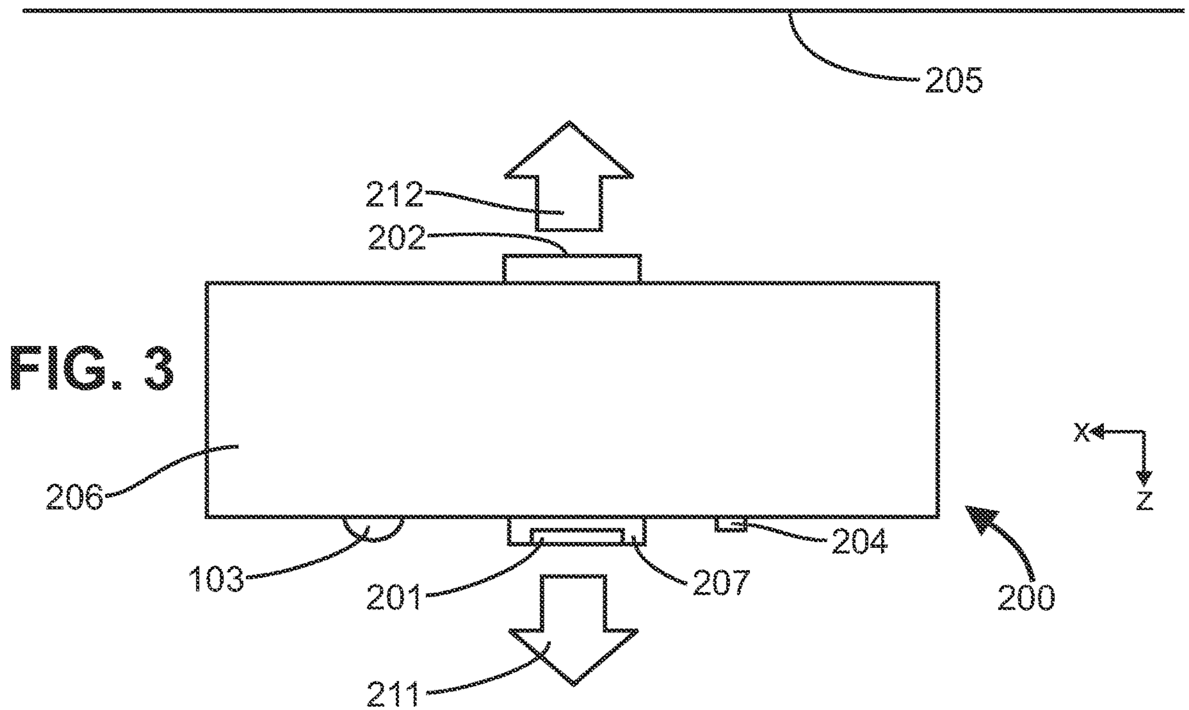
FIG. 3 is a side view of a light emitting device comprising a first UV-C light source emitting UV-C light downward and a second UV-C light source emitting UV-C light upward.

FIG. 3 is a side view of a light emitting device 200 comprising a first UV-C light source 201 comprising one or more first light sources emitting UV-C light 211 downward when the light emitting device 200 is suspended from a ceiling 205 using cables or chain, for example (not shown). The light emitting device 200 also comprises a second UV-C light source 202 comprising one or more second light sources emitting UV-C light 212 upward toward the ceiling 205. The light emitting device 200 further comprises an occupancy sensor 103, a second sensor 204, a housing 206, and an access door 207 to enable access to the first UV-C light source 201 to enable user replacement of the first UV-C light source 201 from beneath the light emitting device 200. In one embodiment, the one or more first light sources emits light with a peak wavelength of 222 nm light and the one or more second light sources emits light with a peak wavelength of 254 nm.

EQUIVALENTS

Those skilled in the art will recognize or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof. This application is intended to cover any adaptations or variations of the specific embodiments discussed herein. Therefore, it is intended that this disclosure be limited only by the claims and the equivalents thereof.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein. Unless indicated to the contrary, all tests and properties are measured at an ambient temperature of 25 degrees Celsius or the environmental temperature within or near the device when powered on (when indicated) under constant ambient room temperature of 25 degrees Celsius.

What is claimed is:

1. A light emitting device comprising:

one or more first light sources emitting a first radiant flux with a peak wavelength within a wavelength range of 220 nanometers and 225 nanometers;

one or more second light sources emitting a second radiant flux with a peak wavelength of 254 nanometers; and one or more visible light emitting sources emitting visible light that provides a visual representation of an angular light spread from the one or more first light sources or the one or more second light sources, wherein the first radiant flux is directed downward, the second radiant flux is directed upward when the light emitting device is suspended or mounted in an environment, and an angular full-width at half-maximum luminous intensity of the visible light is within 20% of an angular full-width at half maximum radiant intensity of the first radiant flux in a light output plane.

2. The light emitting device of claim 1 wherein the first radiant flux has a peak wavelength of 222 nanometers.

3. The light emitting device of claim 2 wherein the one or more first light sources comprise an excimer lamp.

4. The light emitting device of claim 2 wherein the one or more second light sources comprise a mercury vapor lamp.

5. The light emitting device of claim 1 further comprising at least one light detector sensitive to light within a wavelength range of 100 nanometers to 280 nanometers.

6. The light emitting device of claim 1 further comprising at least one motion sensor or occupancy sensor.

7. The light emitting device of claim 1 further comprising a first motion sensor positioned to detect motion below the light emitting device and a second motion sensor positioned to detect motion above the light emitting device wherein the one or more second light sources are turned off when the second motion sensor detects motion above the light emitting device.

8. The light emitting device of claim 1 wherein the light emitting device further comprises an indicator light that emits visible light when the one or more first light sources has reached a time threshold, the time threshold is a threshold less than 30% of an expected lifetime remaining for the one or more first light sources.

9. The light emitting device of claim 1 wherein the first radiant flux from the one or more first light sources divided by the second radiant flux from the one or more second light sources when the one or more first light sources and the one or more second light sources are emitting light at a maximum power allowed by the light emitting device is less than 1.

10. The light emitting device of claim 1 further comprising a fan that directs air from the environment across the second radiant flux.

11. A light emitting device comprising:

one or more first light sources emitting a first radiant flux with a peak wavelength of 222 nanometers at a first duty cycle;

one or more visible light emitting sources emitting visible light that provides a visual representation of an angular light spread from the one or more first light sources or the one or more second light sources; and one or more second light sources emitting a second radiant flux with a peak wavelength of 254 nanometers at a second duty cycle different than the first duty cycle, wherein the first radiant flux is directed downward, the second radiant flux is directed upward when the light emitting device is suspended or mounted in an environment, and an angular full-width at half-maximum luminous intensity of the visible light is within 20% of an angular full-width at half maximum radiant intensity of the first radiant flux in a light output plane.

12. The light emitting device of claim 11 wherein the light emitting device further comprises at least one motion sensor or occupancy sensor and an indicator light that emits visible light when the one or more first light sources has reached a time threshold, the time threshold is a threshold less than 30% of an expected lifetime remaining for the one or more first light sources.

13. The light emitting device of claim 11 wherein the first radiant flux from the one or more first light sources divided by the second radiant flux from the one or more second light sources when the one or more first light sources and the one or more second light sources are emitting light at a maximum power allowed by the light emitting device is less than 1.

14. The light emitting device of claim 11 further comprising a fan that directs air from the environment across the second radiant flux.

15. The light emitting device of claim 11 further comprising at least one motion sensor or occupancy sensor and at least one light detector sensitive to light within a wavelength range of 100 nanometers to 280 nanometers.

16. A method of reducing a pathogenic bioburden in an environment, the method comprising:

suspending or mounting a light emitting device in an environment;

emitting from one or more first light sources a first radiant flux with a peak wavelength within a range of 220 nanometers and 225 nanometers downward into the environment;

emitting from one or more second light sources a second radiant flux with a peak wavelength of 254 nanometers upward into the environment; and emitting visible light from one or more visible light emitting sources that provides a visual representation of an angular light spread from the one or more first light sources or the one or more second light sources, wherein an angular full-width at half-maximum luminous intensity of the visible light is within 20% of an angular full-width at half maximum radiant intensity of the first radiant flux in a light output plane.

17. The method of claim 16 wherein the first radiant flux from the one or more first light sources divided by the second radiant flux from the one or more second light sources when the one or more first light sources and the one or more second light sources are emitting light at a maximum power allowed by the light emitting device is less than 1.

18. The method of claim 17 wherein the one or more first light sources and the one or more second light sources emit light at different duty cycles.

* * * * *